(12) United States Patent
Burkhardt et al.

(10) Patent No.: US 10,094,812 B2
(45) Date of Patent: Oct. 9, 2018

(54) COOKING CONTROL DEVICE, COOKING CONTROL SYSTEM AND COMPUTER PROGRAM PRODUCT

(71) Applicant: AB ELECTROLUX, Stockholm (SE)

(72) Inventors: Jennifer Burkhardt, Rothenburg o. d. Tauber (DE); Kersten Kaiser, Rothenburg o. d. Tauber (DE); Christopher Holm-Hansen, Copenhagen (DK)

(73) Assignee: AB Electrolux, Stockholm (SE)

( * ) Notice: Subject to any disclaimer, the term of this patent is extended or adjusted under 35 U.S.C. 154(b) by 873 days.

(21) Appl. No.: 14/412,101

(22) PCT Filed: Jul. 5, 2013

(86) PCT No.: PCT/EP2013/064275
§ 371 (c)(1),
(2) Date: Dec. 30, 2014

(87) PCT Pub. No.: WO2014/009280
PCT Pub. Date: Jan. 16, 2014

(65) Prior Publication Data
US 2015/0149120 A1 May 28, 2015

(51) Int. Cl.
*A47J 43/28* (2006.01)
*G01N 33/02* (2006.01)
(Continued)

(52) U.S. Cl.
CPC .............. *G01N 33/02* (2013.01); *A47J 36/32* (2013.01); *A47J 43/281* (2013.01); *A47J 45/068* (2013.01);
(Continued)

(58) Field of Classification Search
CPC ......... A47G 21/04; A47J 43/28; G01K 13/00; G01K 1/02; G01N 33/02
See application file for complete search history.

(56) References Cited

U.S. PATENT DOCUMENTS 9,146,147 B1 * 9/2015 Bakhsh .................. A47G 21/02
9,254,099 B2 * 2/2016 Connor ................. A61B 5/1114
9,536,449 B2 * 1/2017 Connor .............. G09B 19/0092

FOREIGN PATENT DOCUMENTS

CN 102106677 6/2011
CN 202069361 12/2011
(Continued)

OTHER PUBLICATIONS https://thetartan.org/2008/11/10/scitech/howthingswork, Amanda Cole, How Things Work: Intelligent Cutlery, Nov. 10, 2008.*
(Continued)

*Primary Examiner* — Huan Tran
(74) *Attorney, Agent, or Firm* — Pearne & Gordon LLP

(57) ABSTRACT

The present invention relates to a cooking control device that comprises sensors (120) and a communication unit (145) to communicate with a display processing device (170). In this manner, taste values of the cooking substance reflecting the current status of the cooking process can be compared with pre-stored taste values representative of a desired cooking result and seasoning advice according to a recipe can be established and presented to a user to converge the cooking status with the desired cooking result.

16 Claims, 4 Drawing Sheets

(51) Int. Cl.
  *A47J 36/32* (2006.01)
  *A47J 45/06* (2006.01)
  *G01D 7/00* (2006.01)
  *G01D 7/12* (2006.01)
  *G01K 1/02* (2006.01)

(52) U.S. Cl.
  CPC ............... *G01D 7/00* (2013.01); *G01D 7/12* (2013.01); *G01K 1/024* (2013.01); *G01K 2207/06* (2013.01); *G01K 2215/00* (2013.01)

(56) References Cited

FOREIGN PATENT DOCUMENTS

| CN | 202255685 | | 5/2012 | |
|---|---|---|---|---|
| CN | 103070622 | * | 5/2013 | .............. A47J 43/28 |
| CN | 203106881 U | * | 8/2013 | .............. A47J 43/28 |
| CN | 203302791 U | * | 11/2013 | .............. A47G 21/04 |

OTHER PUBLICATIONS http://www.goodfoodstl.com/tag/intelligent-spoon/ Kitchen Tools:Calling All Kitchen Geeks Apr. 9, 2015 by Jean Carnahan.*

Cheng C. et al. "Intellegent Spoon", Internet Citation, Apr. 19, 2006. URL: http://www.media.mit.edu/ci/projects/intelligentspoon.html. 1 page.

International Search Report for PCT/EP2013/064275, dated Mar. 21, 2014, 3 pages.

* cited by examiner

COOKING CONTROL DEVICE, COOKING CONTROL SYSTEM AND COMPUTER PROGRAM PRODUCT

In recent times, automation is making more and more inroads into the general household. People want to enjoy their leisure time and while performing daily activities in the household expect more and more support and automation to facilitate their daily activities. In the kitchen, already plenty of appliances are available, such as refrigerators, dishwashers, time and temperature controlled ovens and sophisticated coffee machines. Further, by use of computing tablets and the availability of wide spread wireless LAN installations, people can access all kinds of information on the World-WideWeb. This is also true for the kitchen and cooking area and for recipes.

However, the presence of a recipe doesn't ensure that the food prepared according to the recipe tastes well, or meets the taste expectations of the cook.

Therefore, applicant found that there exists a need to properly control the taste of a meal during cooking and to provide also to an inexperienced cook the possibility to prepare a well tasting meal and in particular a meal which also suits the general taste of the hobby cook.

Already there is some research ongoing in this area. For instance, Cheng, Connie and Leonardo Bonanni have published an internet page related to an "intelligent spoon" working at MIT Medialab: Counter Intelligence Group. Published In Apr. 10, 2008 the link is:

"http://www.media.mit.edu/ci/projects/intelligent-spoon.html"

No other related prior art is known.

The invention is based on the problem to improve the control of the taste of a meal prepared of an average cook.

This problem is solved by a cooking control device according to claim 1, a cooking control system according to claim 10 and a computer program product according to claim 15.

Advantageous further developments of the invention are given in the dependent claims.

Advantageously, the cooking control device according to an embodiment of the present invention allows it to quantify taste properties of a meal and to communicate measured values for further processing in order to control the outcome of the cooking, while at the same time it is independent and can be used like a cooking spoon.

Beneficially, according to a further development of an embodiment of the present invention, energy can be provided by electromagnetic waves. In this manner, the energy source of the cooking control device can be kept small and helps to achieve a good form factor by for instance only including an antenna that receives the electromagnetic waves in the cooking control device.

Favourably, the electromagnetic waves can be received e.g. from an induction coil provided at e.g. an induction oven or hob.

Preferably, according to a further development of an embodiment of the instant invention, energy can be generated on the basis of the temperature difference between the cooking substance and a distant end of the cooking control device that is exposed to room temperature in form of thermo electricity based on the Peltier-Effect.

In this manner, while performing cooking control, energy provision of the cooking control device is self-sustained.

Favourably, according to a further development, the cooking control device has an indicator to indicate at least one cooking control property. In this manner, the cook can focus on the preparation of the meal, while at the same time getting important information about the current status of his meal without having to observe an external display.

Beneficially, according to a further development, an embodiment of the cooking control device has a communication unit that works bidirectional. In this manner, quick external processing of measured values can be provided while at the same time allowing transmission of up to date information to indicate it on the cooking control device.

Favourably, according to a further development of an embodiment of the cooking control device according to the present invention, the communication unit is based on Bluetooth, infrared, near-field communication, general radio, or wireless LAN. In this manner, well-established technical solutions can be used that are widespread and reliable.

Advantageously, according to a further development of an embodiment of the cooking control device according to the present invention, sensors provided on the cooking control device are nano taste receptors.

Beneficially, according to a further development of an embodiment of the cooking control device according to the present invention, the properties of the first and second sensors are selected among sour, salt, bitter, sweet and umami. In this manner, at least two of the tastes perceivable by human taste receptors can be mimicked by the cooking control device and be properly measured in the cooking substance.

Favourably, according to a further development of an embodiment of the cooking control device according to the present invention, the indicator comprises at least one light source. In this manner, low energy consumption of the indicator by using light emitting diodes or optical light emitting diodes can be ensured while at the same time through light intensity, colour or blinking many possibilities for indication of the cooking status are possible.

Favourably, a cooking control system according to the present invention comprises a cooking control device and coupled to it a display processing device. In this manner, the present cooking status can be visualized in a diagram while presenting the current cooking status versus a desired or planned cooking status. Thereby, giving an indication of potential changes to the taste is facilitated and advice about how to achieve a desired cooking result can easily be provided.

Favourably, according to a further development of the cooking control system, the diagram is presented in form of a spiderweb diagram because this allows an easy conceivable presentation of the present cooking status versus the desired or planned taste of the cooking result.

Advantageously, according to a further development of an embodiment of the cooking system according to the present invention, the display processing device comprises a memory for storing cooking information. This allows it to compare pre-stored taste values with taste values present in a currently prepared meal.

Beneficially, according to a further development of an embodiment of the cooking control system according to the present invention, a stored taste value is compared with a taste value received from the cooking control device a difference is established and for a respective taste a cooking recommendation is generated about how to achieve the stored and e.g. desired taste value.

Favourably, according to a further development of an embodiment of the cooking control system according to the present invention, a measured taste value of a finalized meal is stored to use it in the future. For instance, this has the advantage that a user may not wish to adhere to a recipe but instead prefers to adhere to his own modified combination of taste values. In this manner, the cooking control system can be adapted to the individual taste of the cook.

Advantageously, a computer program product according to the present invention allows it to personalize a general personal computer in a manner of a display processing device that is used in the cooking control system of the present invention. In this manner, generally available tablets for instance based on IOS or Android or any kind of Smartphones or Personal Computers can be used in the cooking control system according to the present invention.

Subsequently, the invention will be further explained by giving examples on the basis of embodiments shown in the drawings wherein.

Figure 1:
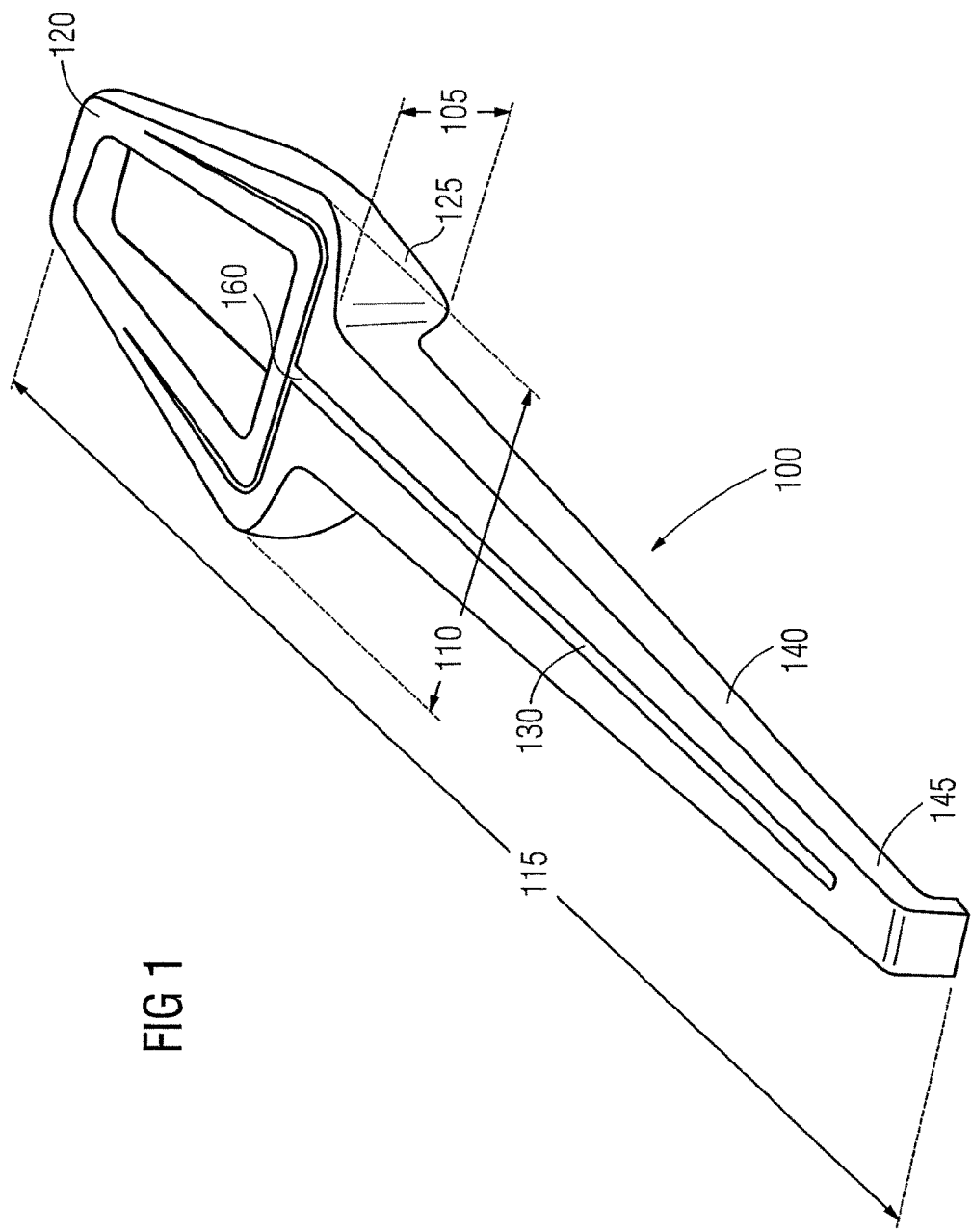
FIG. 1 shows a cooking control device according to an embodiment of the present invention.

As FIG. 1 shows in a preferred embodiment, the cooking control device 100 has a general shape of a spoon. Its length 115 is about 250 mm, its depth 105 is about 20 mm and its width 110 is about 50 mm. At its tip it has sensors 120, preferably nano taste receptors for food tastes that preferably correspond to the taste sensors in the human mouth. Preferably, tastes of salt, umami, sourness, bitterness and sweetness can be sensed. The cooking control device 100 may be equipped with an energy source 125, a processor 160 to quantify the results measured by the sensors; and may be equipped with a communication unit 145 to communicate taste values to the outside. The edges may be made of steel 140 to reinforce the structure of the cooking control device. Preferably, the cooking control device 100 is equipped with an indicator 130 to indicate the current cooking status.

Beneficially, the indicator 130 comprises one or plural LEDs. An indication can then be given in terms of colour to indicate a particular taste or intermittent blinking patterns. Also if plural LEDs are present, a bar chart can be presented to quantify the particular taste value by indicating a percentage of 100% in switching on a corresponding number of LEDs on the cooking control device.

Food is an essential part of our life. It is one of our most basic needs and vital for our wellbeing. It is something that can give us great experiences as well as help us to remember or create new and valid memories. The cooking control device 100 according to an embodiment of the present invention is an intelligent kitchen appliance that assists a user in perfecting his cooking skills and becoming a skilled chef. Thus, it is no longer ones level of cooking expertise, cooking experience or knowledge of taste and spices that defines the outcome of the daily cooking. Instead, the cooking control device 100 personally assists a user in creating perfectly prepared meals. The cooking control device 100 in a non-traditional manner may aid in visualizing the progress of the cooking, aid in enhancing aromas and present results in form of sound, voice and charts while presenting instructions and tips during the cooking process.

For instance, a cook may be able to smell if the steak is seasoned properly, see if a sauce is about to burn to the pan or may get auditory tips on how to enhance the flavours of the specific dish. The sensors 120 e.g. in form of nano taste receptors are state-of-the-art sensor technology and allow to take multiple outputs coming from the food in a continuous fashion during the cooking process. The most important parameters that will e.g. be measured are heat, smell and taste. The cooking control device 100 is able to be used by everyone in a daily dinner cooking. It may however also assist people that cook on a regular basis and eliminate for those people the risk of failure when cooking new dishes.

Sensors 120 among others may include ones capable to determine the salt amount for pasta cooking. Moreover, the sensor may operate by direct contact or indirect by capacitive inductive or optical coupling and measuring frequency and amplitude spectra and then deducing the salt content or any other taste composition.

Sensors 120 may also favourably include temperature and smell sensors. The corresponding power supply of the cooking control device 100 may be established by means of a battery or an inductive field e.g. an extra coil of an induction heater, active or passive RFID. An indicator 130 of the cooking control device 100 may indicate with colour an on and off state, the presence of an optimum cooking state, e.g. optimum salt content of the pasta pot by indicating blue colour, or blinking of an LED, or OLED stripe. The cooking control device 100 further may incorporate a hole at the front tip that is immersed into the cooking substance or may be closed like a spoon. A hole in the front part where the sensors 120 are located helps intensify the exposure of the sensors 120 to the cooking substance because when the cooking substance is stirred with the cooking control device, the substance passes by the sensors in a current. The material composition of a cooking control device 100 should preferably be in a manner that it allows an exposure 120° C. for fluids or up to 300° C. for applications in oil or grease. Further, it should be dishwater-resistant. The communication unit 145 may be operating wireless by Bluetooth or normal radio at 433 MHz/868 MHz/2,4 GHz or WLAN or by infrared or near-field communication (NFC). Also other standard frequency bands, based on the territory of operation, are possible, such as 902 to 928 MHz for North America or South America. A control electronic represented on location by a processor 160 or outside by a display processing device 170 may receive signals from the cooking control device and evaluate the signals leading to a corresponding display function e.g. not enough salt, optimum taste composition. The indicator 130 can be beneficially on the cooking control device 100 itself or on a separate Smartphone or tablet.

Examples of the use of the cooking control device 100 are measuring of grease quality, measuring of salt content, measuring of temperature. Also measuring of taste compositions for instance according certain taste directions is possible e.g. suitable for Asia style, establishing homogeneous balance of tastes, providing season adapted tastes, supplying wellness adapted recipes like e.g. cucumber water; control preparation of diet food for sick persons e.g. few salt with blood pressure; allow alternative sweetening with stevia instead of sugar; assist in preparing mushroom dishes, as some mushrooms are very bitter which can be measured; bitter dishes like zucchini soup can be perfected where the bitterness grade can be measured and can be compensated with spices; also a vinegar content of marinades can be determined for optimizing it by optimizing a sweet-sour relationship; and a long-term preservation can be optimized by establishing a minimum acidity content.

A computer program product 350 according to the present invention can be presented in form of an Application also called "App" at a general App Store available e.g. for "IOS" © or "Android"© general purpose devices.

Humans can recognize basically five different taste sensations bitterness, saltiness, sourness, sweetness and umami. A well cooked and perfectly seasoned meal is usually present when the balance of these five tastes is reached. The five different tastes are present in many unlike ways and can be brought out with a wide variety of items that can be stored in a memory in a cooking control system 200.

Figure 2:
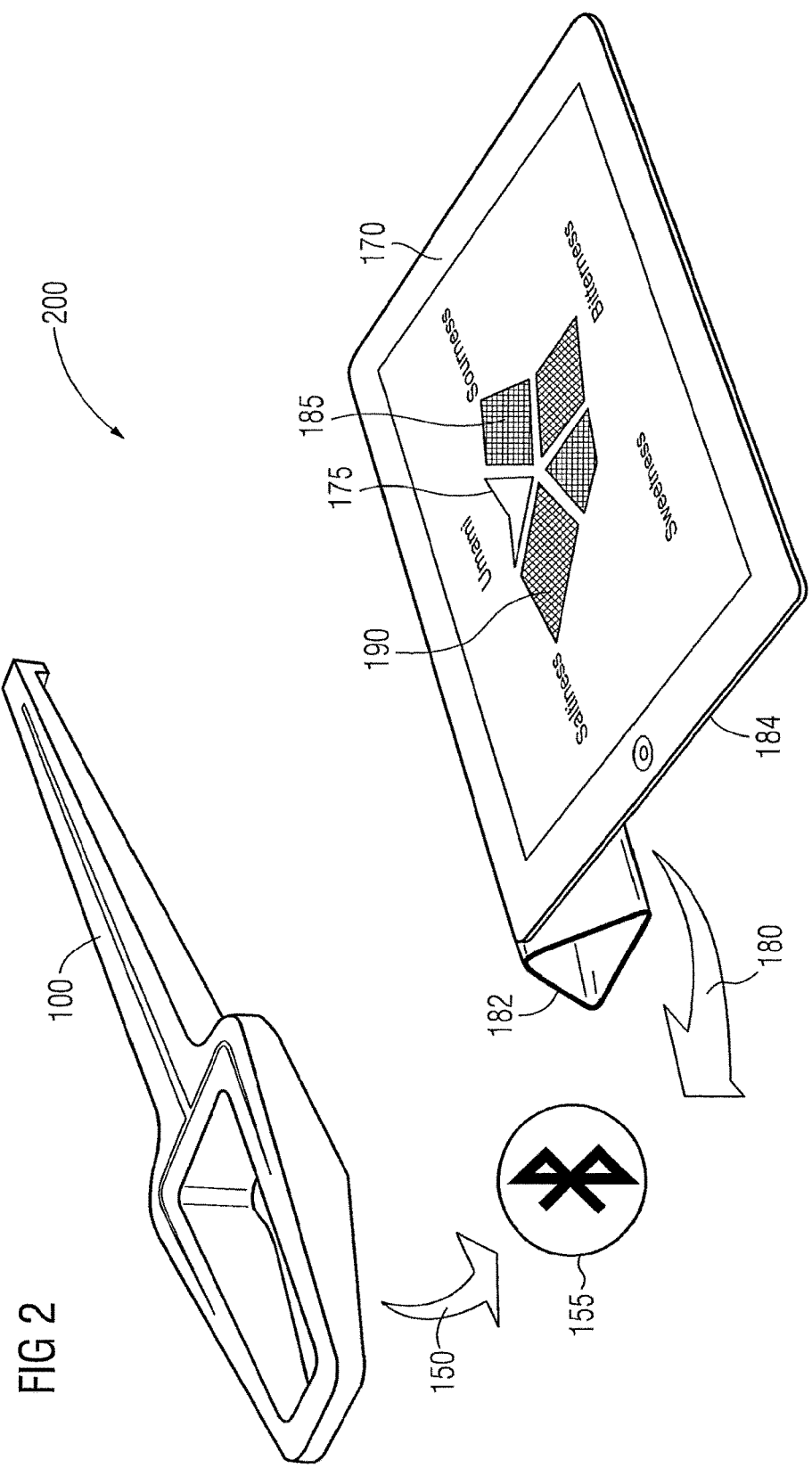
FIG. 2 shows a cooking control system according to an embodiment of the present invention.

FIG. 2 shows an embodiment of a cooking control system 200 according to the present invention. It comprises at least a cooking control device 100 that has been explained in FIG. 1 and a display processing device 170. The display processing device 170 and the cooking control device 100 are preferably coupled by means of a wireless connection indicated by arrows 150 and 180. Here, a Bluetooth symbol 155 is shown. But also infrared, general radio, wireless LAN, near-field communication and the like may be used. The display processing device 170 has a display unit 185 that presents a diagram 175. It may be a tablet computer and include a memory and a processor 182. Here, in this case, the diagram 175 is presented as a spiderweb diagram that shows e.g. the taste value of saltiness 190. This taste value was measured by the sensors 120 of the cooking control device 100 that were immersed into the cooking substance. The display processing device 170 can either be a dedicated device or be a general purpose device like a Smartphone or a tablet that can be personalized by a computer program product as indicated in FIG. 3 by 350, which will e.g. be offered in form of a small application also called App and be available for download over the WorldWideWeb at particular websites.

Figure 3:
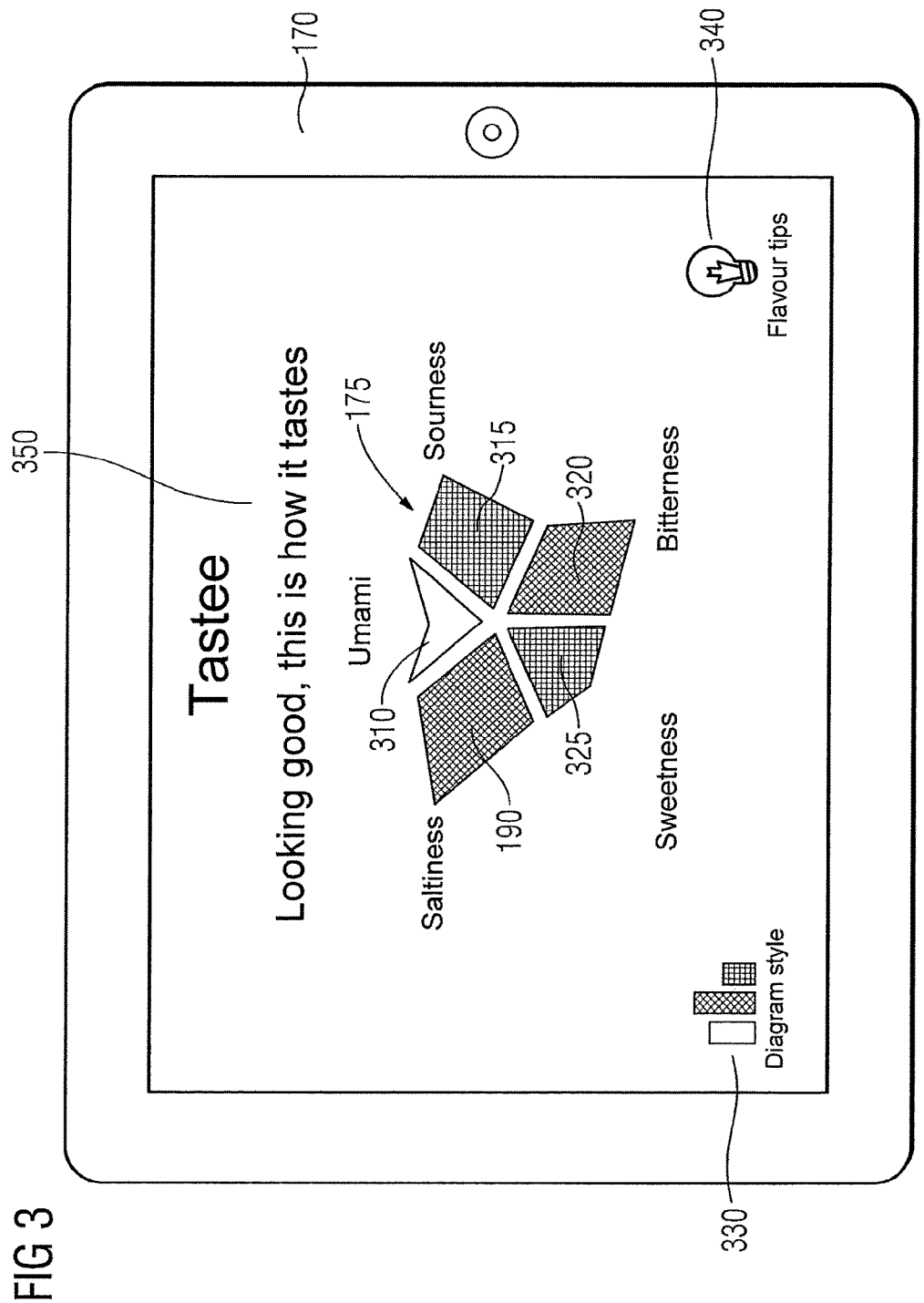
FIG. 3 shows a display processing device according to an embodiment of the present invention.

FIG. 3 shows an example of an embodiment of a display processing device 170. At the display 175 of the display processing device 170, for instance a particular recipe 350 is presented. Below, the current taste status is presented in form of a spiderweb diagram visualizing taste values for saltiness 190, umami 310, sourness 315, bitterness 320 and sweetness 325. The display 175 may be presenting alternative options of diagrams e.g. select a bar chart 330. Further, depending on the current status of the taste values and stored values, e.g. in form of a recipe, a flaw your tip may be given that is indicated at 340. This may allow a user to select particular spices to improve the cooking results. Herein, improving preferably means, that a stored desired profile of taste values is compared to the currently measured taste values. Differences are established and recommendations may be given to minimize the differences by adding certain spices or certain food components. In this manner, the use of spices and flavour enhancers gives the possibility to guide the taste of the food in a direction that is desired. There is no final way of determining what is right, but there is a general understanding of how different traditional dishes should be tasting. E.g. once the cooking control device 100 is immersed into the cooking substance, it may e.g. start transmitting taste values to the display processing device. In the case of a spiderweb diagram, coloured areas for instance will draw out towards the taste areas where the current status of the cooking substance is present. E.g. if assistance or tips for taste enrichment is desired, a push of the button flavour tips 340 e.g. on a touch-screen may present suggestions and ideas how to modify the cooking substance. For instance, a recommendation could be given in order to enrich the umami taste by adding fresh tomatoes into the cooking substance. For measurement e.g. the surface of the cooking control device comprises millions of nano taste receptors marked by 120 in FIG. 1.

Figure 4:
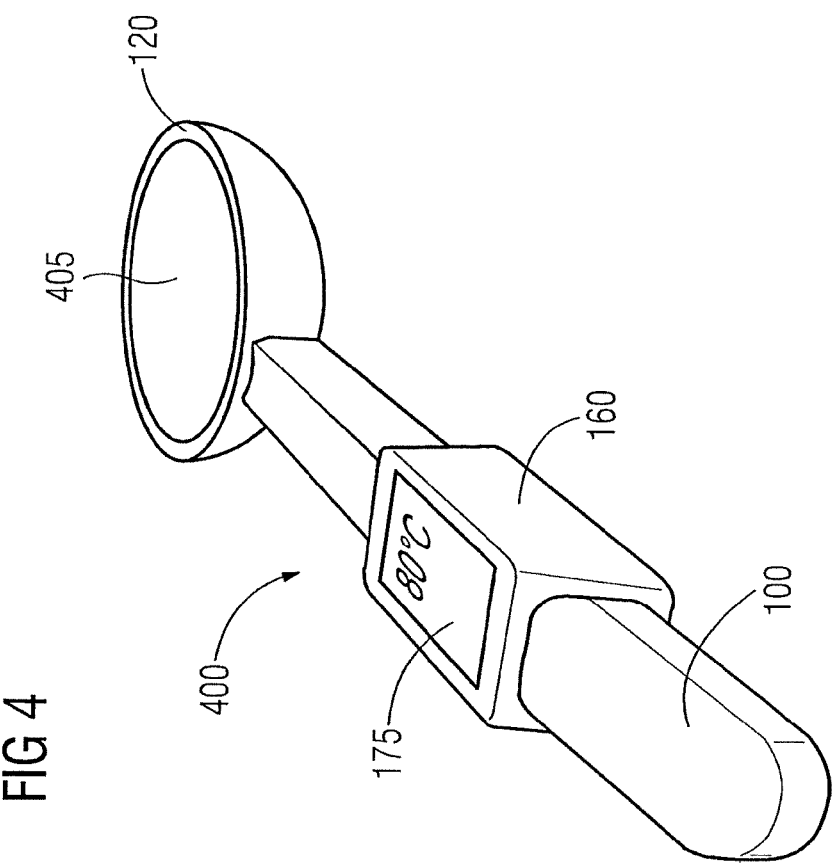
FIG. 4 shows another embodiment of a cooking control device.

FIG. 4 shows another embodiment of a cooking control system 400 according to the present invention. It has a closed spoon area 405, is equipped with taste receptors 120 and presents a display 175 equipped with a processor 160. An advantage of the cooking control system 400 is that it is a single unit design and needs no external communication and processing capabilities.

Figure 5:
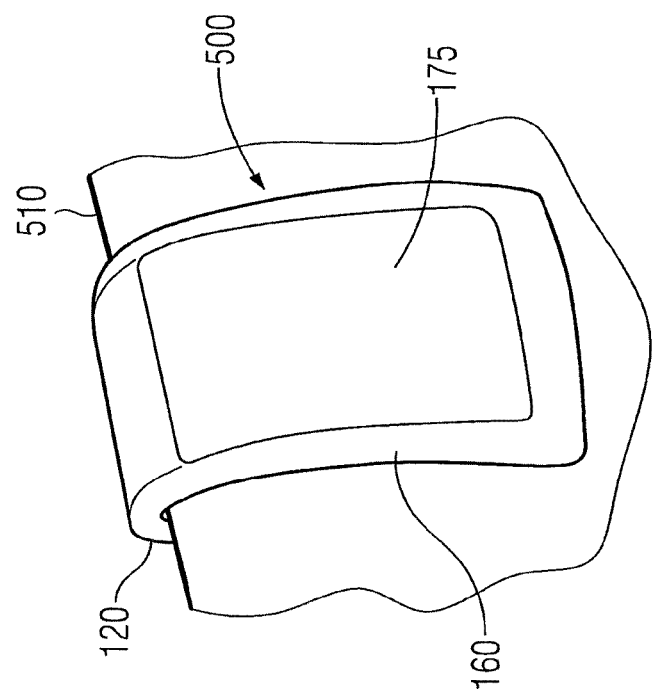
FIG. 5 shows an alternative embodiment of a cooking control device.

Further, FIG. 5 shows a cooking control system 500 that also has a display unit 175, a processor 160 and sensors 120. The cooking control system 500 is e.g. attached to the upper edge 510 of a cook pot.

The sensors 120 may be e.g. exposed to the cooking substance or may work contactless.

LIST OF REFERENCE NUMERALS 100 cooking control device
105 depth
110 width
115 length
120 sensors
125 energy source
130 indicator
140 steel edge
145 communication unit
150 wireless communication from cooking control device
155 type of wireless communication e.g. Bluetooth
160 processor
170 display processing device
175 diagram e.g. spiderweb diagram
180 wireless communication from display processing device
182 processing unit
184 communication unit
185 display unit
190 saltiness;
200 cooking control system
310 umami;
315 sourness;
320 bitterness; and
325 sweetness.
330 diagram style 340: flavour tip;
350 computer program product;
400 integrated cooking control system
405 spoon area
500 alternative cooking control system
510 upper edge of a cook pot.

The invention claimed is:

1. Cooking control device (100, 400, 500) to be at least partially immersed into a cooking substance, the cooking control device comprising:
    a first and a second sensor (120) to measure a respective taste property (190, 310-320) of the cooking substance;
    a processor (160) to quantify the respective taste property into a taste value and prepare it for transmission;
    an energy source (125);
    a bidirectional (150, 180) communication unit (145) communicating the taste values to an external processing unit for cooking control and transmitting processed taste values back to the cooking control device (100, 400, 500).

2. Cooking control device (100, 400, 500) according to claim 1, wherein the energy source (125) is based on reception of electromagnetic waves.

3. Cooking control device (100, 400, 500) according to claim 1, wherein the energy source (125) is based on a temperature gradient between two distant ends of the cooking control device (100, 400, 500).

4. Cooking control device (100, 400, 500) according to claim 1, comprising an indicator (130) for indicating a cooking control property.

5. Cooking control device (100, 400, 500) according to claim 4, wherein the indicator (130) comprises one light source.

6. Cooking control device (100, 400, 500) according to claim 4, wherein the indicator (130) is configured to indicate information received by the bidirectional (150, 180) communication unit (145).

7. Cooking control device (100, 400, 500) according to claim 1, wherein the bidirectional (150, 180) communication unit (145) operates according to Bluetooth, infrared, near-field communication, radio transmission, or wireless LAN.

8. Cooking control device (100, 400, 500) according to claim 1, wherein the sensors (120) are nano taste receptors (120).

9. Cooking control device (100, 400, 500) according to claim 8, wherein the nano taste receptors (120) correspond to food tastes of sour (315), salt (190), bitter (320), sweet (325), and umami (310).

10. Cooking control device (100, 400, 500) according to claim 1, wherein the taste properties (190, 310-320) of the first and second sensors are at least selected among tastes form sour (315), salt (190), bitter (320), sweet (325), and umami (310).

11. Cooking control system (200) comprising a cooking control device (100, 400, 500) according to claim 1; and a display processing device (170) comprising:
   a processing unit (182),
   a communication unit (184); and
   a display unit (185),
   wherein the display processing device (170) receives the taste values from the cooking control device (100, 400, 500) and displays a diagram (175) for cooking control.

12. Cooking control system (200) according to claim 11, wherein the diagram is a spiderweb diagram (175).

13. Cooking control system (200) according to claim 11, wherein the display processing device (170) comprises a memory for storing cooking information;
   wherein a received taste value is compared with a respective stored taste value for cooking control; and
   wherein based on a comparison between the received taste value and the stored taste value an information is generated, which is visibly or audibly displayed.

14. Cooking control system (200) according to claim 11, wherein a cooking recipe is stored in a memory of the display processing device (170); and information is generated to minimize the difference between a respective received and a stored taste value.

15. Cooking control system (200) according to claim 14, wherein a taste value for a finalized cooking substance is stored in the memory for future use.

16. Cooking control system (200) according to claim 11, further comprising an external control device operatively connected to the processing unit (182), the external control device having a memory, an external display, and a computer program product (350) that when loaded into the memory of the external display and executed by the processing unit (182) receives the taste values from the cooking control device (100, 400, 500) and displays the diagram (175) for cooking control instead of the display processing device (170).

* * * * *

UNITED STATES PATENT AND TRADEMARK OFFICE
CERTIFICATE OF CORRECTION

PATENT NO. : 10,094,812 B2
APPLICATION NO. : 14/412101
DATED : October 9, 2018
INVENTOR(S) : Burkhardt et al.

Page 1 of 1

It is certified that error appears in the above-identified patent and that said Letters Patent is hereby corrected as shown below:

On the Title Page

Please add the Foreign Application Priority Data under item (30), to read as follows:

(30) Foreign Application Priority Data
July 9, 2012 (SE) ........................................ 1200431-3

Signed and Sealed this
Tenth Day of September, 2019

Andrei Iancu
*Director of the United States Patent and Trademark Office*